(12) United States Patent
Xu et al.

(10) Patent No.: US 10,458,894 B2
(45) Date of Patent: Oct. 29, 2019

(54) METHODS FOR MONITORING FLUID FLOW AND TRANSPORT IN SHALE GAS RESERVOIRS

(71) Applicant: SCHLUMBERGER TECHNOLOGY CORPORATION, Sugar Land, TX (US)

(72) Inventors: Wenyue Xu, Medford, MA (US); Mery Diaz Campos, Houston, TX (US); Ravinath Kausik Kadayam Viswanathan, Sharon, MA (US)

(73) Assignee: SCHLUMBERGER TECHNOLOGY CORPORATION, Sugar Land, TX (US)

(*) Notice: Subject to any disclaimer, the term of this patent is extended or adjusted under 35 U.S.C. 154(b) by 168 days.

(21) Appl. No.: 15/505,412

(22) PCT Filed: Aug. 12, 2015

(86) PCT No.: PCT/US2015/044795
§ 371 (c)(1),
(2) Date: Feb. 21, 2017

(87) PCT Pub. No.: WO2016/028564
PCT Pub. Date: Feb. 25, 2016

(65) Prior Publication Data
US 2017/0254736 A1    Sep. 7, 2017

Related U.S. Application Data

(60) Provisional application No. 62/040,808, filed on Aug. 22, 2014.

(51) Int. Cl.
*G06F 17/50* (2006.01)
*G06G 7/00* (2006.01)
(Continued)

(52) U.S. Cl.
CPC ............. *G01N 15/08* (2013.01); *E21B 43/00* (2013.01); *E21B 43/12* (2013.01); *E21B 43/26* (2013.01);
(Continued)

(58) Field of Classification Search
CPC ......... G06F 9/445; G01N 15/08; E21B 43/00; E21B 43/12; E21B 43/26; G06G 7/48
(Continued)

(56) References Cited

U.S. PATENT DOCUMENTS 6,018,497 A    1/2000  Gunasekera
6,078,869 A    6/2000  Gunasekera
(Continued)

FOREIGN PATENT DOCUMENTS

WO    WO2004035988 A1    4/2004

OTHER PUBLICATIONS

Akram, A. H. et al.,"Correcting Underestimation of Optimal Fracture Length by Modeling Proppant Conductivity Variations in Hydraulically Fractured Gas Condensate Reservoirs", SPE 100321 presented at the 2006 SPE Gas Technology Symposium held in Calgary, Alberta, Canada, 10 pages.
(Continued)

*Primary Examiner* — Thai Q Phan

(57) ABSTRACT

Methods for analyzing a reservoir in a formation containing hydrocarbon fluid are described. Information characterizing the formation is collected and applied to a formation simulator that is provided with a modified Darcy's law equation that accounts for at least one of gas adsorption/desorption, various modes of diffusive transport, and non-Darcy flow behavior, and the simulator is used to generate indications of the state of the reservoir and/or the state of production of hydrocarbon fluid from the reservoir. The modified Darcy's law equations are particularly useful in analyzing any type
(Continued)

of formation containing any type of hydrocarbon fluid including shale formations containing hydrocarbon gases. According to one embodiment, a dual-porosity shape factor useful in a formation simulator is also provided.

25 Claims, 7 Drawing Sheets

(51) Int. Cl.
| | |
|---|---|
| G01N 15/08 | (2006.01) |
| E21B 43/00 | (2006.01) |
| E21B 43/12 | (2006.01) |
| E21B 43/26 | (2006.01) |
| G01V 99/00 | (2009.01) |
| G06F 9/455 | (2018.01) |
| G06G 7/48 | (2006.01) |

(52) U.S. Cl.
CPC ............ *G01V 99/005* (2013.01); *G06F 9/455* (2013.01); *G06G 7/48* (2013.01)

(58) Field of Classification Search
USPC .......................................... 703/2, 7; 166/266
See application file for complete search history.

(56) References Cited

U.S. PATENT DOCUMENTS

| | | | |
|---|---|---|---|
| 6,106,561 | A | 8/2000 | Farmer |
| 7,441,603 | B2* | 10/2008 | Kaminsky ............ E21B 43/2405 166/266 |
| 7,857,056 | B2* | 12/2010 | Kaminsky ............ E21B 43/2405 166/266 |
| 7,980,312 | B1* | 7/2011 | Hill ......................... E21B 43/24 166/272.2 |
| 8,261,823 | B1* | 9/2012 | Hill ......................... E21B 43/24 166/272.1 |
| 9,085,972 | B1* | 7/2015 | Hill ......................... E21B 43/24 |
| 2007/0023186 | A1* | 2/2007 | Kaminsky ............ E21B 43/2405 166/266 |
| 2009/0038795 | A1* | 2/2009 | Kaminsky ............ E21B 43/2405 166/266 |
| 2010/0057418 | A1 | 3/2010 | Li et al. |
| 2010/0154514 | A1 | 6/2010 | Algive et al. |
| 2014/0122035 | A1 | 5/2014 | Dean et al. |

OTHER PUBLICATIONS

Al-Otaibi, A. M. et al., "Transient Behavior and Analysis of Non-Darcy Flow in Porous and Fractured Reservoirs According to the Barree and Conway Model", SPE 133533 presented at the Western North America Regional Meeting, 2010, 25 pages.
Al-Otaibi, A. M. et al., "An Alternative Approach to Modeling Non-Darcy Flow for Pressure Transient Analysis in Porous and Fractured Reservoirs", SPE 149123 presented at the SPE/DGS Saudi Arabia Section Technical Symposium and Exhibition held in Al-Khobar, Saudi Arabia, 2010, 20 pages.
Aziz, K. et al., "Use of Pressure, Pressure-Squared or Pseudo-Pressure in the Analysis of Transient Pressure Drawdown Data from Gas Wells", Journal of Canadian Petroleum Technology, 1976, 15(2), pp. 58-65.
Azom, P. N. et al., "Dual-Continuum Modeling of Shale and Tight Gas Reservoirs", SPE 159584 presented at the SPE Annual Technical Conference and Exhibition held in San Antonio, Texas, USA, 2012, 22 pages.
Balhoff, M. T. et al., "A Predictive Pore-Scale Model for Non-Darcy Flow in Porous Media" SPE Journal, 2009, 14(4), pp. 579-587.
Barree, R. D. et al., "Beyond Beta Factors: A Complete Model for Darcy Forchheimer, and Trans-Forchheimer Flow in Porous Media", SPE 89325 presented at the SPE Annual Technical Conference and Exhibition held in Houston, Texas, USA, 2004, 8 pages.
Barree, R. D. et al., "Reply to Discussion of Beyond Beta Factors: A Complete Model for Darcy Forchheimer and Trans-Forchheimer Flow in Porous Media", Journal of Petroleum Technology, 2005, 57(8), 73.
Civan, F., "Effective Correlation of Apparent Gas Permeability in Tight Porous Media", Transport in Porous Media, 2010, 82(2), pp. 375-384.
Civan, F. et al., "Shale-Gas Permeability and Diffusivity Inferred by Improved Formulation of Relevant Retention and Transport Mechanisms", Transport in Porous Media, 2011, 86(3), pp. 925-944.
Clarkson, C. R. et al., "Production Analysis of Tight-Gas and Shale-Gas Reservoirs Using the Dynamic-Slippage Concept", SPE Journal, 2012, 17(1), pp. 230-242.
Darabi, H. et al, "Gas Flow in Ultra-Tight Shale Strata", Journal of Fluid Mechanics, 2012, 710, pp. 641-658.
Ertekin, T. et al., "Dynamic Gas Slippage: A Unique Dual-Mechanism Approach to the Flow of Gas in Tight Formations", SPE Formation Evaluation, 1986, 1(1), pp. 43-52.
Fathi, E. et al., "Shale Gas Correction to Klinkenberg Slip Theory", SPE 154977 presented at the SPE Americas Unconventional Resources Conference held in Pittsburgh, Pennsylvania, USA, 2012, 15 pages.
Freeman, C. et al., "Measurement, Modeling, and Diagnostics of Flowing Gas Composition Changes in Shale Gas Wells", SPE 153391 presented at the SPE Latin American and Caribbean Petroleum Engineering Conference held in Mexico City, Mexico, 2012, 25 pages.
Holditch, S. A. et al., "The Effects of Non-Darcy Flow on the Behavior of Hydraulically Fractured Gas Wells", Journal of Petroleum Technology, 1976, 28(10), pp. 1169-1179.
Huang, H. et al., "Modeling Non-Darcy Flow and Perforation Convergence for Vertically Fractured Wells", SPE 107853 presented at the European Formation Damage Conference held in Scheveningen, The Netherlands, 2007, 8 pages.
Huang, H. et al., "Applicability of the Forchheimer Equation for Non-Darcy Flow in Porous Media", SPE Journal, 2008, 13(1), pp. 112-122.
Hubbert, M. K. ,"Darcy's Law and the Field Equations of the Flow of Underground Fluids", SPE 749-G presented at the Darcy Centennial Hydrology Symposium of the International Association of Hydrology held in Dijon, France, 1956, pp. 222-239.
Javadpour, F., "Nanopores and Apparent Permeability of Gas Flow in Mudrocks (Shales and Siltstone)", Journal of Canadian Petroleum Technology, 2009, 48(8), pp. 16-21.
Javadpour, F. et al., "Nanoscale Gas Flow in Shale Gas Sediments", Journal of Canadian Petroleum Technology, 2007, 46(10), pp. 55-61.
Klinkenberg, L. J., "The Permeability of Porous Media to Liquids and Gases", presented at the API 11th Mid Year Meeting held in Tulsa, Oklahoma, May; in API Drilling and Production Practice (1941), pp. 200-213.
Lai, B. et al, "Non-Darcy Porous Media Flow According to the Barree and Conway Model: Laboratory and Numerical Modeling Studies", SPE 122611 presented at the SPE Rocky Mountain Petroleum Technology Conference held in Denver, Colorado, USA, 2009, 15 pages.
Langmuir, I., "The Constitution and Fundamental Properties of Solids and Liquids. Part I. Solids" The Journal of the American Chemical Society, 1916, 38(2), pp. 2221-2295.
Langmuir, I., "The Adsorption of Gases on Plane Surfaces of Glass, Mica and Platinum", The Journal of the American Chemical Society, 1918, 40(9), pp. 1361-1403.
Ling, K. et al., "Determining Coefficient of Quadratic Term in Forchheimer Equation", IPTC 16582 presented at the International Petroleum Technology Conference held in Beijing, China, 2013, 9 pages.
Macini, P. et al., "Laboratory measurements of non-Darcy flow coefficients in natural and artificial unconsolidated porous media", Journal of Petroleum Science and Engineering, 2011, 77(3), pp. 365-374.

(56) References Cited

OTHER PUBLICATIONS

Martins, J. P. et al., "The Effects of Non-Darcy Flow in Propped Hydraulic Fractures", SPE 20709 presented at the SPE Annual Technical Conference and Exhibition held in New Orleans, Louisiana, USA, 1990, 15 pages.
Maxwell, J. C., "On the dynamical theory of gases", Philosophical Transactions of the Royal Society of London, 1867, 157, pp. 49-88.
Maxwell, J. C., "On stresses in rarified gases arising from inequalities of temperature", Philosophical Transactions of the Royal Society of London, 1879, 170, pp. 231-256.
Michel, G. G. et al, "Parametric Investigation of Shale Gas Production Considering Nano-Scale Pore Size Distribution, Formation Factor, and Non-Darcy Flow Mechanisms", SPE 147438 presented at the SPE Annual Technical Conference and Exhibition held in Denver, Colorado, USA, 2011, 20 pages.
Miskimins, J. L. et al., "Non-Darcy Flow in Hydraulic Fractures: Does It Really Matter?", SPE 96389 presented at the SPE Annual Technical Conference and Exhibition held in Dallas, Texas, USA, 2005, 8 pages.
Noman, R. et al., "Transition from Laminar to Non-Darcy Flow of Gases in Porous Media" in Advances in Core Evaluation: Accuracy and Precision in Reserves Estimation, Reviewed Proceedings of the First Society of Core Analysts European Core Analysis Symposium held in London, United Kingdom, 1990, pp. 447-462.
Olson, K. E. et al., "Multiphase Non-Darcy Pressure Drop in Hydraulic Fracturing", SPE 90406 presented at the SPE Annual Technical Conference and Exhibition held in Houston, Texas, USA, 2004, 13 pages.
Ozkan, E. et al., "Modeling of Fluid Transfer from Shale Matrix to Fracture Network", SPE 134830 presented at the SPE Annual Technical Conference and Exhibition held in Florence, Italy, 2010, 18 pages.
Rahmanian, M. et al., "A New Unified Diffusion—Viscous-Flow Model Based on Pore-Level Studies of Tight Gas Formations", SPE Journal, 2012, 18(1), pp. 38-49.
Raijo, T., "Correction of non-Darcy Coefficient and How to Estimate It for Development Wells", SPE 145852 presented at the SPE Asia Pacific Oil and Gas Conference and Exhibition held in Jakarta, Indonesia, 2011, 11 pages.
Roy, S. et al., "Modeling Gas Flow through Microchannels and Nanopores", Journal of Applied Physics, 93(8), pp. 4870-4879.
Sakhaee-Pour, A. et al., "Gas Permeability of Shale", SPE Reservoir Evaluation & Engineering, 2012, 15(4), pp. 401-409.
Shi, J. et al., "Diffusion and Flow Mechanisms of Shale Gas through Matrix Pores and Gas Production Forecasting", SPE 167226 presented at the SPE Canadian Unconventional Resources Conference held in Calgary, Alberta, Canada, 2013, 19 pages.
Singh, H. et al., "Nonempirical Apparent Permeability of Shale", SPE 168724 presented at the Unconventional Resources Technology Conference held in Denver, Colorado, USA, 2013, 16 pages.
Smith, M. B. et al., "An Investigation of Non-Darcy Flow Effects on Hydraulic Fractured Oil and Gas Well Performance", SPE 90864 presented at the SPE Annual Technical Conference and Exhibition held in Houston, Texas, USA, 2004, 14 pages.
Swami, V. et al., "A Pore Scale Gas Flow Model for Shale Gas Reservoir", SPE 155756 presented at the SPE Americas Unconventional Resources Conference held in Pittsburgh, Pennsylvania, USA, 2012, 16 pages.
Swami, V. et al., "Non-Darcy Flow in Shale Nanopores: Do We Have a Final Answer?", SPE 162665 presented at the SPE Canadian Unconventional Resources Conference held in Calgary, Alberta, Canada, 2012, 17 pages.
Van Batenburg, D. et al., "Discussion of SPE 89325, Beyond Beta Factors: A Complete Model for Darcy, Forchheimer, and Trans-Forchheimer Flow in Porous Media", Journal of Petroleum Technology, 2005, 57(8), pp. 72-74.
Vincent, M. C. et al., "Non-Darcy and Multiphase Flow in Propped Fractures: Case Studies Illustrate the Dramatic Effect on Well Productivity", SPE 54630 presented at the 1999 SPE Western Regional Meeting held in Anchorage, Alaska, USA, 14 pages.
Wang, F. et al., "A Method to Determine the Turbulence Coefficient of High Rate Gas Reservoir", Advanced Materials Research, 2013, 616-618, pp. 917-923.
Wu, Y.-S. et al., "A Unified Mathematical Model for Unconventional Reservoir Simulation", SPE 142884 presented at the SPE EUROPEC/EAGE Annual Conference and Exhibition held in Vienna, Austria, 2011, 16 pages.
Xu, W. et al., "Quick Estimate of Initial Production from Stimulated Reservoirs with Complex Hydraulic Fracture Network", SPE 146753 presented at the SPE Annual Technical Conference and Exhibition held in Denver, Colorado, USA, 2011, 13 pages.
Zhang, F. et al., "Determination of Fracture Conductivity in Tight Formations with Non-Darcy Flow Behaviour", SPE 162548 presented at the SPE Canadian Unconventional Resources Conference held in Calgary, Alberta, Canada, 2011, 21 pages.
International Preliminary Report on Patentability of International Patent Application No. PCT/US2015/044795, dated Mar. 9, 2017, 6 pages.

* cited by examiner

METHODS FOR MONITORING FLUID FLOW AND TRANSPORT IN SHALE GAS RESERVOIRS

PRIORITY

The application claims priority from U.S. Ser. No. 62/040,808, filed Aug. 22, 2014, the complete disclosure of which is hereby incorporated by reference herein.

FIELD

The subject disclosure generally relates to methods and systems for assessing hydrocarbon reservoirs and for performing wellsite operations. More particularly, the subject disclosure relates to methods for assessing shale gas reservoirs by utilizing reservoir models, and for monitoring fluid flow and transport in shale gas reservoirs although the disclosure is not limited thereto and may be used to assess and monitor fluid flow in any reservoir.

BACKGROUND

In the development of oil and gas fields, it is common to quantify hydrocarbon fluid flow and transport using a reservoir simulator. For example, ECLIPSE™ (a trademark of Schlumberger) is an oil and gas reservoir simulator that provides a high resolution reservoir model that simulates fluid flow and mass transport in highly complex, variably saturated conditions. ECLIPSE, which is described in co-owned U.S. Pat. Nos. 6,018,497, 6,078,869 and 6,106,561 which are hereby incorporated by reference herein in their entireties, can couple geomechanical modeling with fluid flow. ECLIPSE can also perform fluid flow predictions. Other simulators similarly model fluid flow in formations during production.

ECLIPSE and other simulators typically utilize the well-known continuity equation based on Darcy's law that has been broadly used by reservoir engineers of the oil and gas industry for many years with various degrees of success. The great boom story of North America shale gas exploitation has seen an extension of the use of the same continuity equation from the simulation of conventional gas reservoirs to the simulation of unconventional reservoirs containing formation matrices of extremely-low permeability and extremely small pore sizes imbedded with highly conductive hydraulic fractures. While the continuity equation is being used in these unconventional reservoirs, the limitations of the continuity equation with respect to unconventional reservoirs have been documented. The issue is further complicated by the existence of highly permeable hydraulic fracture of fracture network in an extremely low permeable reservoir. At the center of the issue is the validity or accuracy of the Darcy's law in quantifying gas transport both in low permeability formation matrix and through highly permeable fractures.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

The subject disclosure relates to methods of assessing shale gas reservoirs and for performing wellsite operations through the use of a reservoir model that accounts for fluid flow and transport in shale gas reservoirs.

In one aspect, a reservoir is investigated and measurements are conducted and the properties of the reservoir such as reservoir porosity and permeability and the properties of reservoir fluids are characterized. The properties are then inferred over a grid in a reservoir simulator that accounts for the transport of fluid mass, energy and momentum in a shale reservoir during production. In particular, in addition to accounting for the commonly adopted Darcy fluid flow and transport models which are accounted for by existing reservoir simulators, the simulator of the subject disclosure also accounts for the mechanisms such as gas adsorption/desorption, hydrocarbon molecular diffusion, effect of pore size on hydrocarbon transport (Knudsen diffusion, Klinkenberg effect), non-Darcy flow behavior (due to high flow velocity, rapid variation of flow velocity and fluid density in space and in time) and thermal constraint on gas adsorption/desorption, fluid flow and transport processes. In this manner, hydrocarbon production from a shale gas reservoir is monitored and analyzed, and appropriate decisions regarding production are made.

In one aspect, an analytical solution of isothermal gas transport through a shale formation matrix is given and used to obtain a generalized dual-porosity shape factor that is both consistent with existing models and more rigorous in accounting for the effects of time-dependent fluid pressure. The method can be implemented into existing reservoir simulators, for applications to shale gas reservoirs, with or without the presence of hydraulic fracture or fracture network. It can also be used as an independent tool for surveillance, forecasting and optimization of production from shale gas reservoirs, with or without the presence of hydraulic fracture or fracture network. It can be applied to other types of hydrocarbon reservoirs upon further simplification or modification.

Further features and advantages of the subject disclosure will become more readily apparent from the following detailed description when taken in conjunction with the accompanying drawings.

BRIEF DESCRIPTION OF THE DRAWINGS

The subject disclosure is further described in the detailed description which follows, in reference to the noted plurality of drawings by way of non-limiting examples of the subject disclosure, in which like reference numerals represent similar parts throughout the several views of the drawings, and wherein.

DETAILED DESCRIPTION

Figure 1:
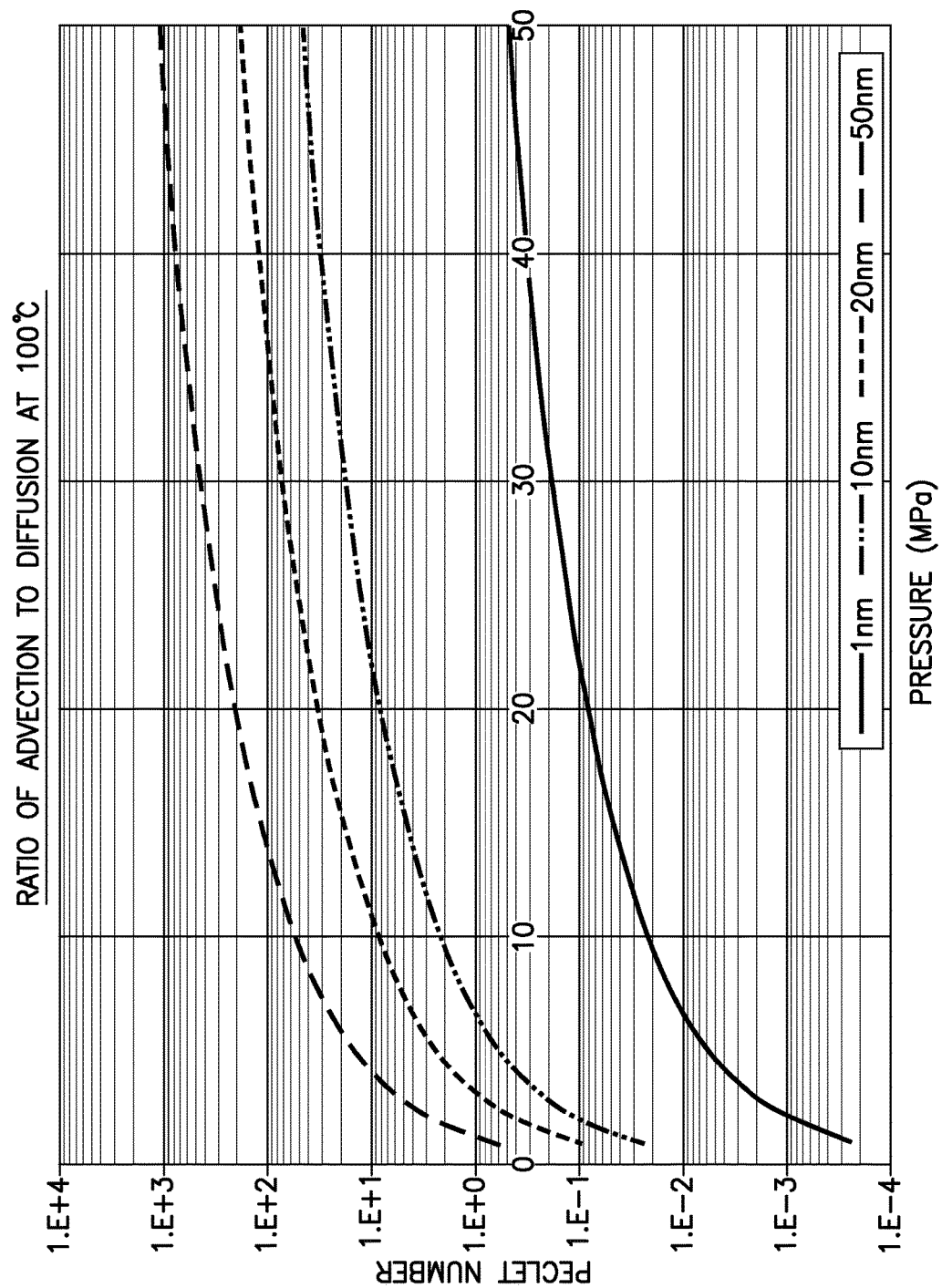
FIG. 1 is a graph showing the contribution of the advective transport of methane relative to that of the diffusive transport expressed in terms of the Peclet number (ratio of advection to diffusion) for several pore sizes as a function of fluid pressure at temperature 100° C.

The particulars shown herein are by way of example and for purposes of illustrative discussion of the examples of the subject disclosure only and are presented in the cause of providing what is believed to be the most useful and readily understood description of the principles and conceptual aspects of the subject disclosure. In this regard, no attempt is made to show structural details in more detail than is necessary, the description taken with the drawings making apparent to those skilled in the art how the several forms of the subject disclosure may be embodied in practice. Furthermore, like reference numbers and designations in the various drawings indicate like elements.

In embodiments, methods for determining hydrocarbon storage and transport in shale reservoirs are described. The methods include accounting for the transport due to viscous flow and molecular diffusion and the effect of molecular collisions with pore walls, inertial forces and heat transport, and hydrocarbon storage variation due to gas adsorption or desorption; and are constructed utilizing mass, energy and momentum conservation laws. Isothermal flow and transport of a single component gas is used as an example for the sake of mathematical simplicity and may be extended to more complicated situations involving a multiphase multicomponent fluid mixture. In one aspect, the use of empirical parameters is limited to as few as possible. The methods may be applied to a reservoir formation block or blocks bounded by a single fracture, by parallel fractures, by two perpendicular sets of parallel fractures or by three perpendicular sets of parallel fractures. The methods may be applied to improve existing conventional reservoir simulators or to develop tools for production forecasting, surveillance and optimization.

As will be appreciated by those of skill in the art, to date in the oil and gas industry, gas flow from reservoir rock to the wellbore has been regarded as isothermal, and properties of the gas are treated as functions of fluid pressure p. The well-known transport equation for the flow of a gas, with density $\rho_g$ and viscosity $\mu_g$, through reservoir rock, with connected porosity $\phi$ and permeability k, is given by $$\frac{\partial(\phi\rho_g)}{\partial t} - \nabla \cdot \left(\frac{\rho_g k}{\mu_g} \nabla p\right) = 0 \quad (1)$$

where the contribution of the gravitational force is neglected for simplicity; although the gravitational term and hydraulic head may be used in lieu of pressure. The transport equation may be posed as a diffusion equation in terms of w for isothermal gas flow, $$\frac{\partial \omega}{\partial t} - \nabla \cdot (\kappa \nabla \omega) = 0 \quad (2)$$

where $$\omega = \phi \rho_g \quad (3)$$

is the new dependent property for the amount of gas stored in pore space, $$\kappa = \frac{k}{\phi c_t \mu_g} \quad (4)$$

is the effective diffusivity of property ω and $$c_t = \frac{1}{\phi \rho_g} \frac{\partial(\phi\rho_g)}{\partial p} = c_\phi + c_g, \ c_\phi = \frac{1}{\phi}\frac{\partial \phi}{\partial p}, \ c_g = \frac{1}{\rho_g}\frac{\partial \rho_g}{\partial p} \quad (5)$$

where $c_t$, $c_\phi$ and $c_g$ are respectively the total compressibility, the pore compressibility and the gas compressibility. It will be appreciated that equation (2), together with definitions (3) to (5), involves fewer approximations or mathematical complexity than its counterparts posed in terms of either pressure, pressure-squared or pseudo-pressure.

Equation (2), together with properly set initial and boundary conditions of the reservoir, can be solved for property ω and, hence, fluid pressure or density as a function of time and space. However, transport equations (1) and (2) are overly simplified and often deviate from the conservation laws applicable to hydrocarbon flow and transport in a shale reservoir.

In one embodiment, in order to more accurately account for gas transport in shale reservoirs during production, the contribution to gas transport due to molecular diffusion (which is usually negligible in conventional reservoirs) is added as described hereinafter. In one embodiment, in order to more accurately account for gas transport in shale reservoirs during production, the effect of gas molecule collision with the pore walls is added as described hereinafter as is the contribution of diffusive gas transport. In one embodiment, in order to more accurately account for gas transport in shale reservoirs during production, the contribution of gas adsorption/desorption is added as set forth hereinafter as are the effect of gas molecule collision with the pore walls and the contribution of diffusive gas transport.

Turning first to the contribution of diffusive gas transport, it will be appreciated that there are primarily two fundamental modes of fluid transport in porous media; namely the advective mode resulting from viscous fluid flow and the diffusive mode resulting from molecular diffusion. Transport equation (1) or (2) accounts for the advective fluid transport but neglects any diffusive contribution. While this approximation is reasonable for liquid hydrocarbon reservoirs and gas reservoirs having a medium to high permeability, in one aspect, it is considered insufficient for gas transport in shale. In one embodiment, to account for the diffusive transport, the transport equation (2) is modified to have the same form but with a new effective diffusivity $$\kappa = \frac{k_{app}}{\phi c_t \mu_g} \quad (6)$$

where the apparent permeability $k_{app}$ is defined by $$k_{app} = k\left[1 + \frac{16 D_g \mu_g (1 + c_g p)}{d_p^2 p}\right], \quad (7)$$

where $d_p$ is the effective or representative pore size of the shale, $D_g$ is the molecular diffusivity, corresponding to the random thermal motion of hydrocarbon molecules between their consecutive collisions to each other, and the second term on the right hand side of the equation (7) is a diffusive transport term. FIG. 1 plots the contribution of the advective transport of methane relative to that of the diffusive transport expressed in terms of the Peclet number (i.e., the ratio of advection to diffusion) for several pore sizes as a function of fluid pressure at temperature 100° C. The contribution of diffusive transport is certainly not negligible for shale reservoirs, especially at lower pressures. Thus, according to one embodiment, a reservoir simulator is provided with a modified effective diffusivity using an apparent permeability as set forth in equations (6) and (7), and which, in the case of shale reservoirs containing gas, will cause the reservoir simulator to provide different results than would otherwise be obtained.

Turning next to the effect of gas molecule collision with the pore walls, it will be appreciated that the size of the pores in a shale matrix is quite small (anywhere from nanometers to micrometers) compared to that of the other reservoir types. This wall effect on the advective transport is quantified by a multiplier $W_A$ (which is a function of the Knudsen number $K_N$ described hereinafter) to the advective transport so that equation (7) can be extended so that the apparent permeability used in transport equation (2) becomes $$k_{app} = k\left[W_A(K_N) + \frac{16D_g\mu_g(+c_g p)}{d_p^2 p}\right] \quad (8)$$

with $$W_A(K_N) = \left[\frac{16}{3}\left(\frac{2}{\alpha}-1\right)K_N + \left(1-\frac{4}{3}K_N\right)^2\right]\left(1-\frac{4}{3}K_N\right)^2 H\left(1-\frac{4}{3}K_N\right) \quad (9)$$

where $\alpha$ is the fraction of diffuse reflection of molecules after their collision with pore wall and has a value close to 1, and $$K_N = \frac{\lambda}{d_p} \quad (10)$$

is the Knudsen number and $\lambda$ is the mean free path of gas molecules defined as $$\lambda = \frac{2\sqrt{2}\,m_g}{\pi\sigma^2 \rho_g} \quad (11)$$

where $m_g$ is the molecular mass and $\sigma$ is the diameter of the gas molecules. The wall effect on the diffusive transport is quantified by another multiplier $W_D$ (which is also a function of the Knudsen number) to the molecular diffusivity so that the apparent permeability used in transport equation (2) (via equation (6)) becomes $$k_{app} = k\left[W_A(K_N) + \frac{16D_g W_D(K_N)\mu_g(1+c_g p)}{d_p^2 p}\right] \quad (12)$$

with $$W_D(K_N) = \begin{cases} 1, & K_N \leq \frac{1}{2} \\ \frac{1}{2}E(K_N) + \frac{1}{4K_N}, & K_N > \frac{1}{2} \end{cases} \quad (13)$$

where $$W(K_N) = 1 - \left(1 - \frac{1}{4K_N^2}\right)^{3/2} + \frac{3}{4K_N^2}\left(\arcsin\frac{1}{2K_N} + \sqrt{4K_N^2 - 1} - \frac{\pi}{2}\right) \quad (14)$$

Figure 2:
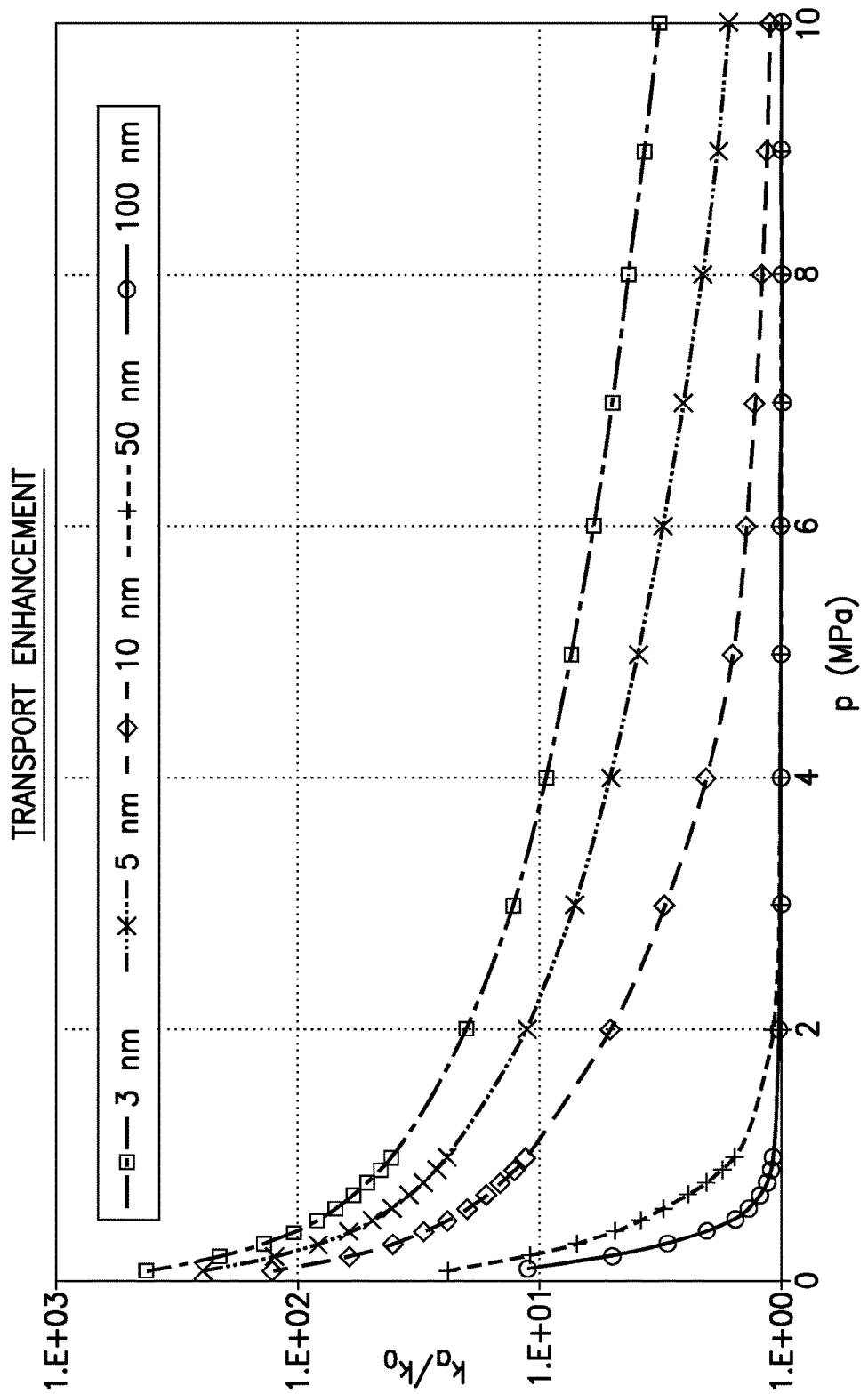
FIG. 2 is a graph showing enhancement to total methane transport (including both advective and diffusive transports) due to the wall effect.

FIG. 2 plots the enhancement to methane transport due to the wall effect, expressed in terms of the ratio of apparent permeability to intrinsic permeability, for several pore sizes as a function of fluid pressure at temperature 100° C. Thus, according to one embodiment, a reservoir simulator is provided with a modified apparent permeability according to equations (6) and (8)-(14), which in the case of shale reservoirs containing gas will cause the reservoir simulator to provide different results than would otherwise be obtained.

Figure 3:
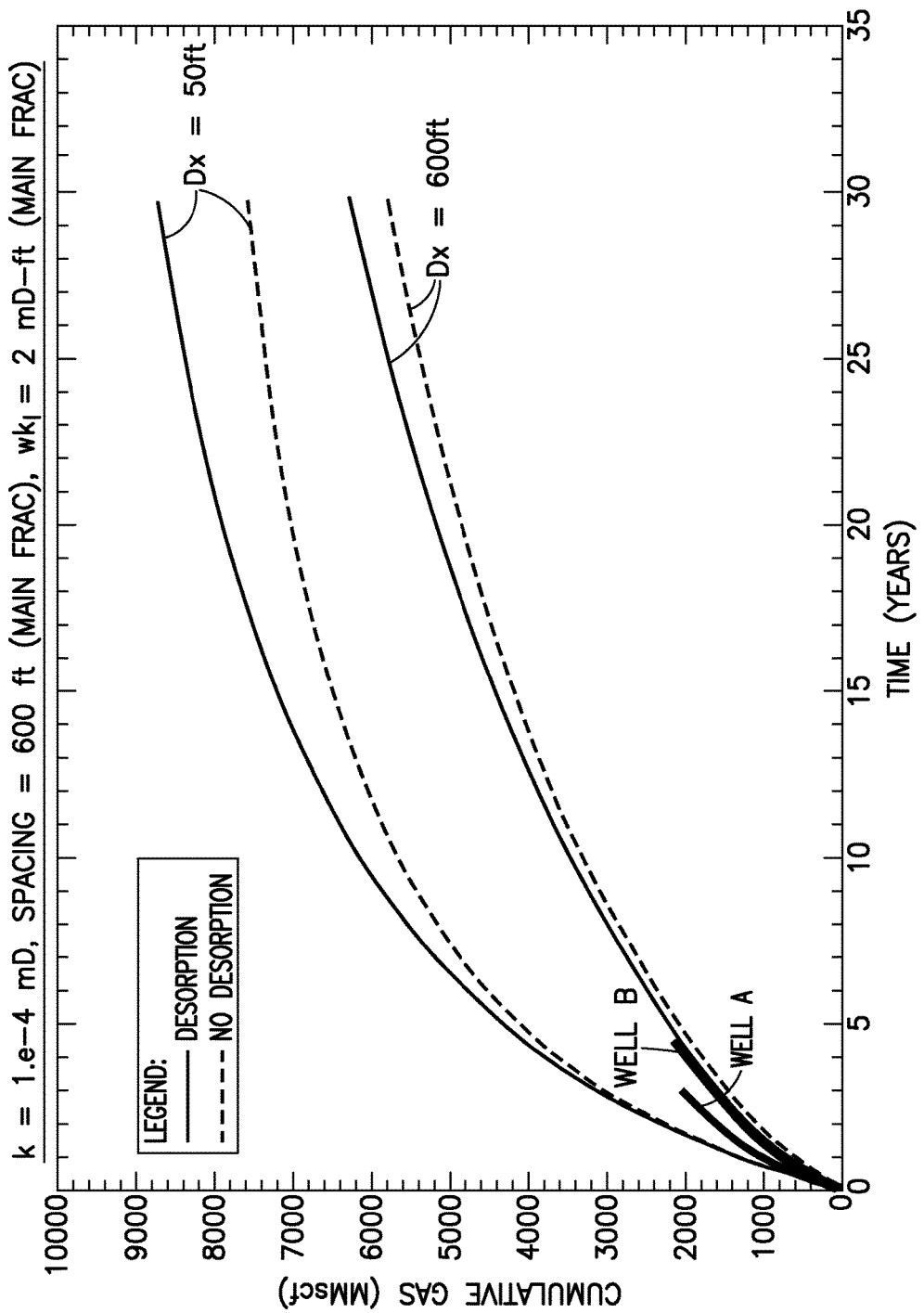
FIG. 3 is a graph showing production increase due to release of adsorbed gas.

Another effect on gas production from shale reservoirs comes from gas adsorption/desorption taking place mostly in organic matter in shale. This effect is accounted for by the same transport equation (2) with a modified property $$\omega = \phi\rho \quad (15)$$

where $$\rho = (1-V_a)\rho_g + V_a\rho_a \quad (16)$$

is the mixture density of the free gas and the adsorbed gas, and $\rho_a$ and $V_a$ are respectively the density and the volume fraction of the adsorbed gas. The pore volume fraction $V_a$ of adsorbed gas is related to the commonly used total volume $V_{ads}$ of adsorbed gas via $$V_{ads} = \phi V_a \quad (17)$$

which may be quantified via a Langmuir isotherm $$V_{ads} = V_{ac}(T)\frac{B(T)p}{1+B(T)p} \quad (18)$$

where B is the 'relative life' of a molecule of adsorbed gas and $V_{ac}$ is the maximum total volume of adsorbed gas, both measured at temperature T. In addition, the effective diffusivity of equation (6) is modified by a further extended apparent permeability $$k_{app} = k\left[W_A(K_N) + \frac{16D_g W_D(K_N)\mu_g(1+c_g p)}{d_p^2 p}\right]\frac{\rho_g(1-V_a)}{\rho} \quad (19)$$

and total effective compressibility $$c_t = \frac{\rho_g(c_g+c_\phi)}{\rho} + \frac{V_a}{\rho}\left[\rho_a c_a - \rho_g c_g + \frac{\rho_a - \rho_g}{(1+Bp)p}\right] \quad (20)$$

where $$c_a = \frac{1}{\rho_a}\frac{\partial \rho_a}{\partial p} \quad (21)$$

is the compressibility of the adsorbed gas. FIG. 3 demonstrates an increase in cumulative gas production due to adsorbed gas of a Barnett shale reservoir. Thus, according to one embodiment, a reservoir simulator is provided with a modified apparent permeability and total compressibility according to equations (6) and (15)-(21), which in the case of shale reservoirs containing gas will cause the reservoir simulator to provide different results than would otherwise be obtained.

Despite the complexities introduced thus far, the concept of the original Darcy's law as a rectilinear relationship between the gas transport and the hydraulic head gradient is still valid. More particularly, gas transport in shale reservoirs with the added complexities discussed so far can still be described by a diffusion equation such as equation (2) with an effective diffusivity $\kappa$ defined by equation (6), but modified to use an apparent permeability $k_{app}$ defined by equation (19) and a total compressibility $c_t$ defined by equation (20).

According to one aspect, one challenge to the applicability of the original Darcy's law to gas flow in shale formations stems from the requirement of satisfying the law of momentum conservation, which is of particular interest when fluid flow changes rapidly either in space or time, such as might occur in places near a wellbore or along or near the surface of a fracture. The law of momentum conservation for an inertia volume in space states that the rate of increase of the momentum in the volume equals the rate of momentum generation (or the sum of external forces acting on the fluid) in the volume plus the rate of momentum transported into the volume minus the rate of momentum transported out of the volume. More particularly, $$-\phi\left(\nabla p + \frac{\mu_g}{k_{app}}\vec{v}\right) = \frac{\partial(\phi\rho_g\vec{u})}{\partial t} + \nabla \cdot (\phi\rho_g\vec{u}\vec{u}) \qquad (22)$$

$$= \vec{u}\frac{\partial(\phi\rho_g)}{\partial t} + \phi\rho_g\frac{\partial \vec{u}}{\partial t} + \vec{u}\nabla \cdot (\phi\rho_g\vec{u}) + \nabla\vec{u} \cdot (\phi\rho_g\vec{u})$$

where $\vec{u}$ is the interstitial fluid velocity while $\vec{v}$ is the apparent Darcy velocity. Due to the law of fluid mass conservation $$\frac{\partial(\phi\rho_g)}{\partial t} + \nabla \cdot (\phi\rho_g\vec{u}) = \frac{\partial(\phi\rho_g)}{\partial t} + \nabla \cdot (\rho_g\vec{v}) = 0 \qquad (23)$$

equation (22) reduces to $$-\left(\nabla p + \frac{\mu_g}{k_{app}}\vec{v}\right) = \rho_g\frac{\partial \vec{u}}{\partial t} + \rho_g\vec{u} \cdot \nabla \vec{u} = \frac{\rho_g}{\phi}\frac{D\vec{v}}{Dt} \qquad (24)$$

which indicates that Darcy's Law is substantially exact if the effect of both temporal and spatial changes in fluid flow is zero or negligible. Even if the effect is not negligible, equation (24) for the law of fluid momentum conservation may still be nominally written into the form of a Darcy's law $$\vec{v} = -\frac{k_m}{\mu_g}\nabla p \qquad (25)$$

with a modified permeability $k_m$ replacing the apparent permeability $k_{app}$ used by the effective diffusivity $\kappa$ defined by equation (6). For instance, the modified permeability for one-dimensional flow is $$k_m = k_{app}\left(1 - \frac{k_{app}\rho_g}{\phi\mu_g v}\frac{Dv}{Dt}\right) \qquad (26)$$

In one embodiment, to account for the non-Darcy effect, the apparent permeability $k_{app}$ appearing in the effective diffusivity $\kappa$ defined by equation (6) may be replaced by this modified permeability $k_m$ in order to use equation (1) or (2) for gas flow and transport in a shale reservoir, and a reservoir simulator provided with this modified transport equation will cause the reservoir simulator to provide different results than would otherwise be obtained in the case of shale reservoir containing gas where the standard Darcy's law is utilized. A more rigorous approach to account for the non-Darcy effect is to simultaneously solve the coupled conservation equations (2) of mass (still using the apparent permeability $k_{app}$) and (24) of momentum together.

In one aspect, the previous analysis and equations apply to isothermal gas flow, which does not account for the law of energy conservation. However, under certain circumstances, the effect of heat transport on gas storage and transport in shale reservoirs can be significant. For instance, a rapid drop in fluid pressure and resultant expansion in gas volume across a fracture surface may lead to a substantial drop in fluid temperature, which may result in a change in fluid properties and, hence, may impact the gas flow itself. Another process, which is endothermic and particularly relevant to gas production from shale reservoirs, is gas desorption. Methods developed to date to account for the contribution of gas desorption have been based on various forms of the Langmuir isotherm of equation (18). Langmuir desorption implicitly assumes instantaneous gas desorption in responding to a pressure drop with unlimited rate of heat supply. This is reasonable in cases of a slow pressure drop over a long period of time. Generally speaking, the rate of gas adsorption/desorption is constrained by a limited rate of mass and heat transport in shale. According to one embodiment, one way to more accurately account for the contribution of gas desorption to shale reservoir production is to use the governing equation (2) of gas transport in conjunction with a governing equation for associated heat transport.

More particularly, assuming the heat transport occurs at conditions close to local thermodynamic equilibrium, the governing equation for heat transport may be obtained from the law of energy conservation as $$\frac{\partial}{\partial t}[\phi\rho h + (1-\phi)\rho_s h_s] + \nabla \cdot (\rho_h h_g \vec{v} - \lambda\nabla T) = 0 \qquad (27)$$

where $\lambda$ is the effective heat conductivity, $\rho_s$ and $h_s$ are the density and enthalpy of the shale matrix, $h_g$ is the enthalpy of the free gas phase, and $$\rho h = (1-V_a)\rho_g h_g + V_a\rho_a h_a, \qquad (28)$$

$$\rho = (1-V_a)\rho_g + V_a\rho_a, \qquad (29)$$

where $h_a$ is the enthalpy of adsorbed gas. Both the density and enthalpy of the free gas and the adsorbed gas are a function of temperature T and pressure p, while the density and enthalpy of the mixture of free and adsorbed gases are also functions of the volume fraction $V_a$ of the adsorbed phase. Equation (27) may be solved for either enthalpy h or temperature T. In order to quantify the rate of gas adsorption/desorption, the knowledge about the thermodynamic equilibrium between the gaseous and adsorbed phases is required. For a single component gas, the p-T adsorption/desorption boundary and density and enthalpy of the two coexistent phases are obtained. If the gas comprises multiple components, a p-T-$V_a$ relationship for adsorption/desorption of the gas mixture is needed. Mass and momentum transport equations should also be added for each of the gas components.

In Aziz, K., et al., "Use of Pressure, Pressure-Squared or Pseudo-Pressure in the Analysis of Transient Pressure Drawdown Data from Gas Wells", *Journal of Canadian Petroleum Technology* PETSOC-76-02-06 (1976), it was observed that the analytical solution of governing equation (2), given for radial flow due to constant-rate production from infinite-acting reservoirs, with a constant diffusivity κ calculated at an averaged pressure, is a good approximation to the accurate numerical solution corresponding to a κ as a function that varies over the whole reservoir. In one embodiment, analytical solutions of equation (2) are provided with flexible time-dependent boundary conditions corresponding to a broad range of production scenarios. It is assumed that these solutions are a good approximation when a similarly averaged κ is used. Thus, equation (2) is rewritten $$\frac{\partial \omega}{\partial t} - \frac{\partial}{\partial x}\left(\kappa \frac{\partial \omega}{\partial x}\right) = 0 \tag{30}$$

for linear flow, or $$\frac{\partial \omega}{\partial t} - \frac{1}{r}\frac{\partial}{\partial r}\left(\kappa r \frac{\partial \omega}{\partial r}\right) = 0 \tag{31}$$

for radial flow (without fractures). With respect to production via radial flow toward the wellbore, the state-of-the-art analytical solutions of the radial flow problem were obtained either for a constant production rate or for a constant pressure drop at the wellbore. In one embodiment methods are disclosed for an arbitrarily time-dependent ω (or fluid pressure p, as ω is a unique function of p). The mathematical problem of radial isothermal fluid flow with arbitrarily time-dependent ω at the wellbore is $$\frac{\partial \omega}{\partial t} - \frac{1}{r}\frac{\partial}{\partial r}\left(\kappa r \frac{\partial \omega}{\partial r}\right) = 0 \tag{32}$$

$$\omega(0, r) = \omega_0(r)$$

$$\omega(t, 0) = \omega_w(t)$$

$$\frac{\partial \omega(t, r)}{\partial r}\bigg|_{r\to\infty} = 0.$$

Its solution was found to be $$\omega(t, r) = \omega_0(r) - [\omega_0(r) - \omega_w(t)]\frac{Ei(-s)}{Ei(-s_w)} \tag{33}$$

where $$Ei(x) = -\int_{-x}^{\infty}\frac{e^{-u}}{u}du \tag{34}$$

$$s = \frac{r^2}{4\kappa t} \text{ and } s_w = \frac{r_w^2}{4\kappa t}. \tag{35}$$

The solution reduces to $$\omega(t, r) = \omega_r - [\omega_r - \omega_w(t)]\frac{Ei(-s)}{Ei(-s_w)} \tag{36}$$

if $$\omega_0(r) = \omega_r. \tag{37}$$

The rate of fluid flowing into the wellbore can thus be obtained by $$q_w = 2\pi h r_w \kappa \frac{\partial \omega}{\partial r}\bigg|_{r=r_w} = -4\pi h \kappa [\omega_r - \omega_w(t)]\frac{e^{-s_w}}{Ei(-s_w)} \tag{38}$$

where h is the thickness of the producing reservoir formation. In another embodiment methods are disclosed for an arbitrarily time-dependent production rate q. The mathematical problem of radial isothermal fluid flow with arbitrarily time-dependent q at the wellbore is $$\frac{\partial \omega}{\partial t} - \frac{1}{r}\frac{\partial}{\partial r}\left(\kappa r \frac{\partial \omega}{\partial r}\right) = 0 \tag{39}$$

$$\omega(0, r) = \omega_0(r)$$

$$-2\pi h \kappa \left[r\frac{\partial \omega}{\partial r}\right]_{r=r_w} = q_g(t)$$

$$\left[\frac{\partial \omega}{\partial r}\right]_{r\to\infty} = 0$$

The solution for ω was found to be $$\omega = \omega_0(r) + \frac{q_g(t)}{4\pi h \kappa}e^{s_w}Ei(-s) \tag{40}$$

Figure 4:
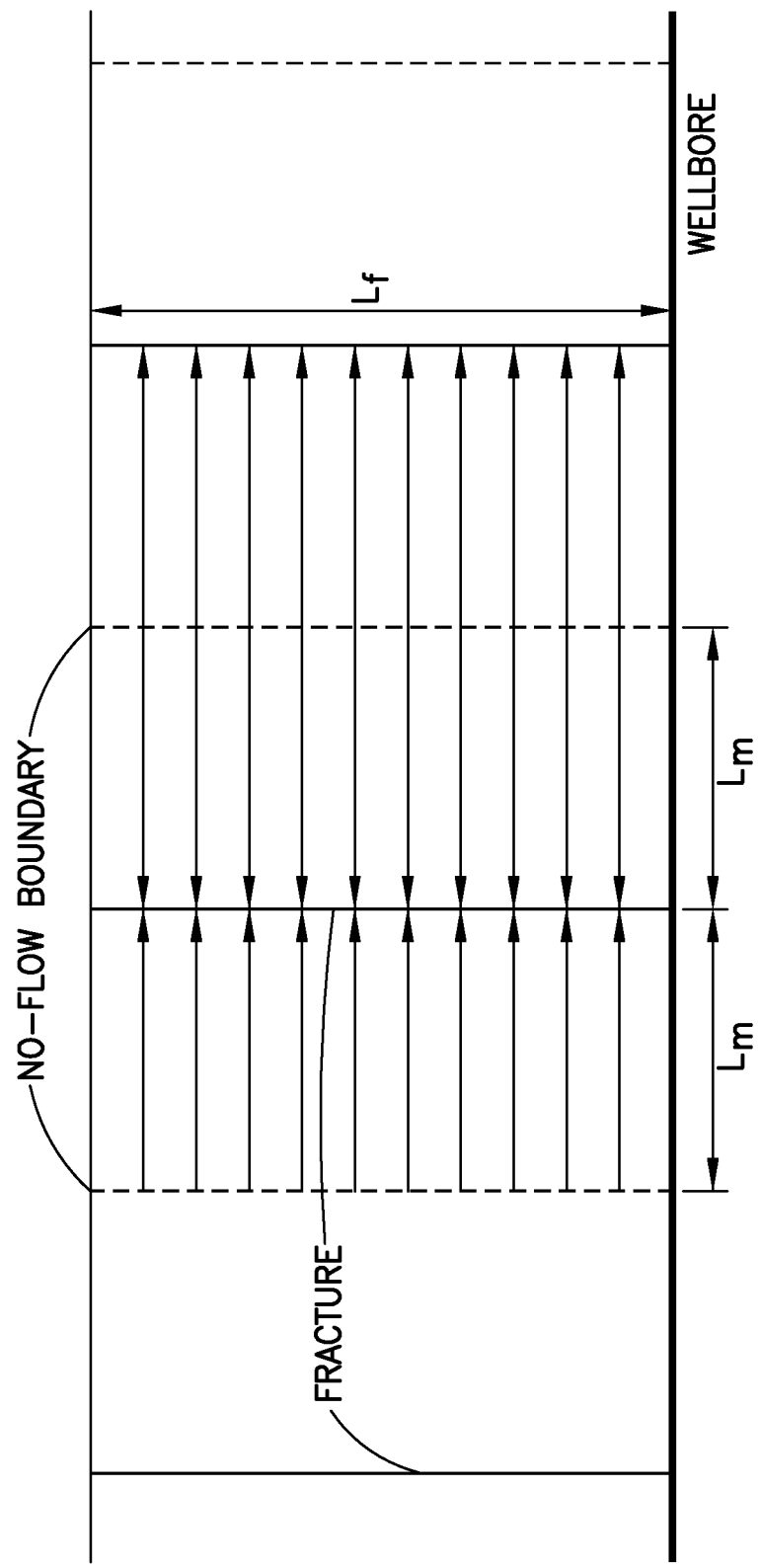
FIG. 4 depicts top view of a horizontal well intersected by multiple hydraulic fractures and with lighter arrows indicating gas flow.

FIG. 4 illustrates scenarios of gas flow through a reservoir formation and fractures during production from a shale reservoir. With respect to production via a single planar hydraulic fracture such as suggested in FIG. 4 where the central fracture is bounded on each side by no-flow boundaries, gas flows laterally into the fracture before it flows horizontally in the fracture towards the wellbore. The initial and boundary conditions for 1D gas flow perpendicular to the fracture in a semi-infinite space are $$\omega(0, x) = \omega_0(x) \tag{41}$$

$$\omega(t, 0) = \omega_f(t)$$

$$\frac{\partial \omega(t, x)}{\partial x}\bigg|_{x\to\infty} = \frac{\partial \omega_0(x)}{\partial x}\bigg|_{x\to\infty}.$$

The solution of equation (30) satisfying conditions (41) was given by Xu, W., et al., "Quick Estimate of Initial Production from Stimulated Reservoirs with Complex Hydraulic Fracture Network", *SPE* 146753 presented at the SPE Annual Technical Conference and Exhibition held in Denver, Colo., USA, 30 Oct. 2011):

$$\omega(t, x) = \tag{42}$$
$$\omega_0(x) + \frac{x}{2\sqrt{\pi\kappa}} \int_0^t \omega_f(u)(t-u)^{-3/2} e^{-\frac{x^2}{4\kappa(t-u)}} du - \omega_0(0)\text{erfc}\left(\frac{x}{2\sqrt{\kappa t}}\right)$$

which reduces to $$\omega(t, x) = \omega_r \text{erf}\left(\frac{x}{2\sqrt{\kappa t}}\right) + \frac{x}{2\sqrt{\pi\kappa}} \int_0^t \omega_f(u)(t-u)^{-3/2} e^{-\frac{x^2}{4\kappa(t-u)}} du \tag{43}$$

if $$\omega_0(x) = \omega_r. \tag{44}$$

The rate of gas flowing into the fracture can thus be obtained by $$q_g = \kappa \frac{\partial \omega}{\partial x}\bigg|_{x=0} = -\phi \sqrt{\frac{\kappa}{\pi}} \int_0^t \frac{1}{\sqrt{t-u}} \frac{d\omega_f(u)}{du} du. \tag{45}$$

Horizontal fluid flow along the planar fracture (in the y-direction perpendicular to the x-direction) of height $h_f$ and width $w_f$ is described by $$\frac{\partial(\phi_p \rho_g h_f w_f)}{\partial t} - \frac{\partial}{\partial y}\left(\frac{\rho_g h_f w_f k_p}{\mu_g} \frac{\partial p_f}{\partial y}\right) = 2 q_g h_f \tag{46}$$

together with proper initial and boundary conditions, where $\phi_p$ and $k_p$ are the proppant pack porosity and permeability, respectively. Equation (46) may be solved numerically and coupled with the analytical solutions (42) and (45). At any given time, t+Δt, fracture pressure $p_f$ can be obtained by solving equation (46) using $q_g$ calculated based on the history of the fracture pressure, which is in turn calculated by equation (45).

Gas flow from a shale reservoir with a vertical planar fracture in the middle and bounded by two non-flow boundaries at distance $L_m$ (as in FIG. 4) is described here by:

$$\frac{\partial \omega}{\partial t} - \kappa \frac{\partial^2 \omega}{\partial x^2} = 0 \tag{47}$$

$$\omega(0, x) = \omega_r$$

$$\omega(t, L_m) = \omega_f(t)$$

$$\frac{\partial \omega}{\partial x}\bigg|_{x=0} = 0$$

Its solution is given by $$\omega(t, x) = \omega_f(t) - \frac{2}{L_m} \sum_{i=0}^{\infty} \frac{(-1)^i}{C_i} \cos(C_i x) f_i(t) \tag{48}$$

where $$f_i(t, L_m) = \int_0^t e^{-C_i^2 \kappa(t-u)} \frac{d\omega_f}{dt}\bigg|_{(u)} du \tag{49}$$

and $$C_i = \frac{(2i+1)\pi}{2L_m} \tag{50}$$

Consequently the rate of gas flow across a fracture surface can be calculated by $$q_g(t) = -\frac{2\kappa}{L_m} \sum_{i=0}^{\infty} f_i(t). \tag{51}$$

Gas flow along the fracture is again described by equation (46). This solution is also applicable to situations where a shale reservoir is embedded with several equally spaced parallel vertical planar fractures as in FIG. 4. The gas flow through the fractures can be described by equation (46) together with proper initial and boundary conditions. Similar to the single fracture cases, equations (46) and (51) can be coupled and solved for fluid pressure distribution along the fractures as a function of time.

Figure 5:
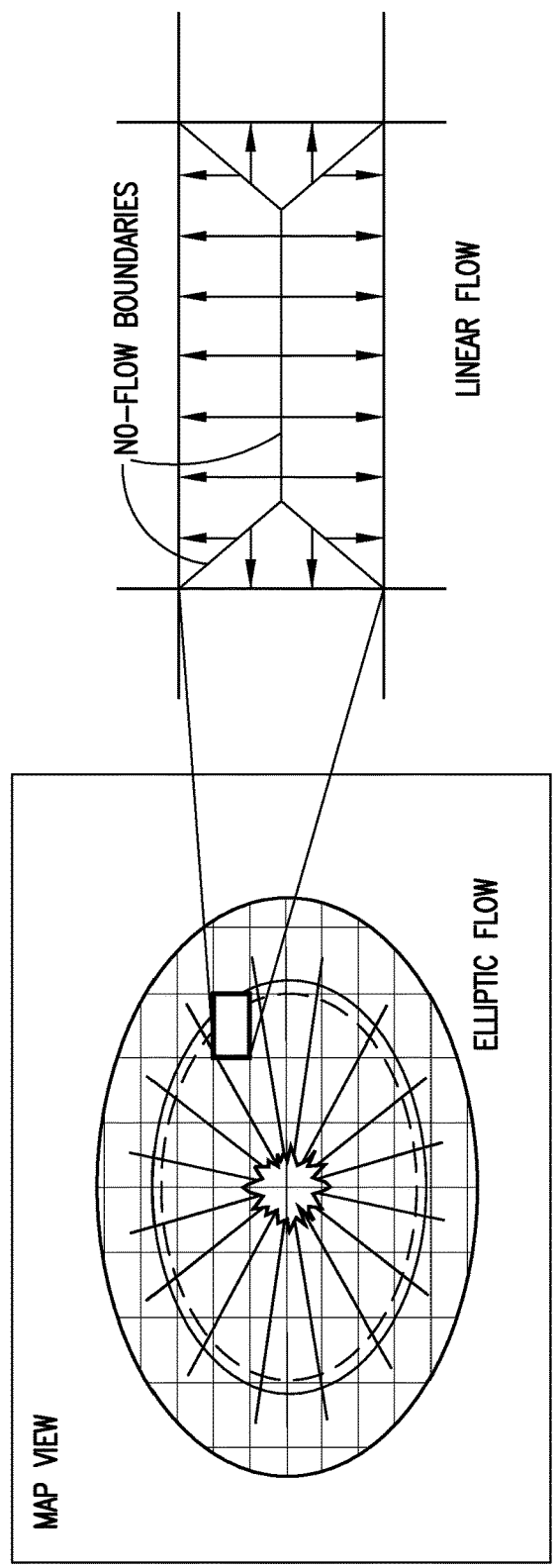
FIG. 5 depicts top view of gas flow during production, where the gas flows from the reservoir matrix into the fracture network and then, in an effective manner, flows elliptically across the fracture network into the wellbore.

Turning now to FIG. 5, an elliptical wiremesh-like fracture network, intersected by a wellbore near its center, is seen embedded in a shale reservoir. The fracture network includes two perpendicular sets of parallel vertical planar fractures, each respectively with equal half-spacing $L_1$ and $L_2$ ($L_2 \geq L_1$) and with a highlighted block broken out and shown magnified. According to previously referenced Xu et al. (2011), the governing equation for gas flow towards the wellbore through the elliptical fracture network of height $h_{fn}$ is $$\frac{\partial \omega_{fn}}{\partial t} - \frac{4}{\pi x h_{fn}} \frac{\partial}{\partial x}\left(x h_{fn} \kappa_{fn} \frac{\partial \omega_{fn}}{\partial x}\right) = q_m \tag{52}$$

where x is the coordinate along the major axis of the fracture network, $q_m$ is the rate of gas flowing into the fracture network from the shale matrix blocks bounded by the fractures, $$\phi_{fn} \approx \frac{\phi_p}{2}\left(\frac{w_{f1}}{L_1} + \frac{w_{f2}}{L_2}\right), \tag{53}$$

and $$\kappa_{fn} = \frac{k_{fx} w_{fx}}{2 L_{fx} \phi_{fn} \mu_g c_g}, \tag{54}$$

where $w_{fx}$ and $k_{fx}$ are the width and permeability of the fracture along the major axis, $L_{fx}$ is the half-spacing between fractures parallel to the x-axis, $L_{f1}$ and $L_{f2}$ are respectively the half-spacing of the fracture set 1 and set 2.

According to one aspect, the fractured reservoir may be viewed as a dual-porosity porous medium. The governing equation (52) for such a dual-porosity reservoir becomes $$\frac{\partial \omega_{fn}}{\partial t} - \frac{4}{\pi x h_{fn}} \frac{\partial}{\partial x}\left(x h_{fn} \kappa_{fn} \frac{\partial \omega_{fn}}{\partial x}\right) = \sigma \kappa_m(\omega_m - \omega_{fn}) \tag{55}$$

where $\kappa_m$ is an averaged property defined by equation (6) (as further defined, if desired, by one of equations (7), (12) or (19)) for the shale matrix, and where $\omega_m$ is an averaged property defined by equation (15) for the shale matrix. The shape factor σ can be derived using analytical solutions (48) and (51) and based on the symmetric nature of the linear gas flow towards the boundaries of a matrix block, as indicated by FIG. 5. The shape factor σ thus obtained is $$\sigma = \frac{6\sqrt{\pi\kappa_m}\sum_{n=0}^{\infty}C_n(L_1)a_n(t,L_1) - \frac{L_2+2L_1}{L_1}\sum_{n=0}^{\infty}b_n(t,L_1) - 6\sum_{n=0}^{\infty}f_n(t,L_1)}{\left[\frac{L_2}{L_1}\sum_{n=0}^{\infty}\frac{f_n(t,L_1)}{C_n^2(L_1)} - 4\sqrt{\pi}\,\kappa_m^{3/2}\sum_{n=0}^{\infty}C_n(L_1)c_n(t,L_1) + \frac{L_2+2L_1}{L_1}\kappa_m\sum_{n=0}^{\infty}d_n(t,L_1) + 4\kappa_m\sum_{n=0}^{\infty}e_n(t,L_1)\right]} \quad (56)$$

where $$a_n(t,L_1) = \int_0^t \sqrt{t-u}\,\operatorname{erfc}\left[C_n(L_1)\sqrt{\kappa_m(t-u)}\right]\frac{d\omega_{fn}}{dt}\bigg|_{(u)} du \quad (57)$$

$$b_n(t,L_1) = \int_0^t Ei[-C_n^2(L_1)\kappa_m(t-u)]\frac{d\omega_{fn}}{dt}\bigg|_{(u)} du$$

$$c_n(t,L_1) = \int_0^t (t-u)^{3/2}\operatorname{erfc}\left[C_n(L_1)\sqrt{\kappa_m(t-u)}\right]\frac{d\omega_{fn}}{dt}\bigg|_{(u)} du$$

$$d_n(t,L_1) = \int_0^t (t-u)Ei[-C_n^2(L_1)\kappa_m(t-u)]\frac{d\omega_{fn}}{dt}\bigg|_{(u)} du$$

$$e_n(t,L_1) = \int_0^t (t-u)e^{-C_n^2(L_1)\kappa_m(t-u)}\frac{d\omega_{fn}}{dt}\bigg|_{(u)} du$$

and $$C_n(L_1) = \frac{(2n+1)\pi}{2L_1} \quad (58)$$

In one aspect, equations (55) and (56) (and associated equations (57) and (58)) may be utilized by a reservoir simulator to further define hydrocarbon fluid (e.g., gas) flow in the fractured reservoir. More particularly, equations (55)-(58) which are particularly useful in assessing a fractured reservoir containing gas (although they are not limited thereto), may be used alone with equation (2) by a reservoir simulator, or may be used in conjunction with equation (6) and any of equations (7), (12), or (19) or equations (25) and (26) which also relate to assessing a gas reservoir.

Figure 6:
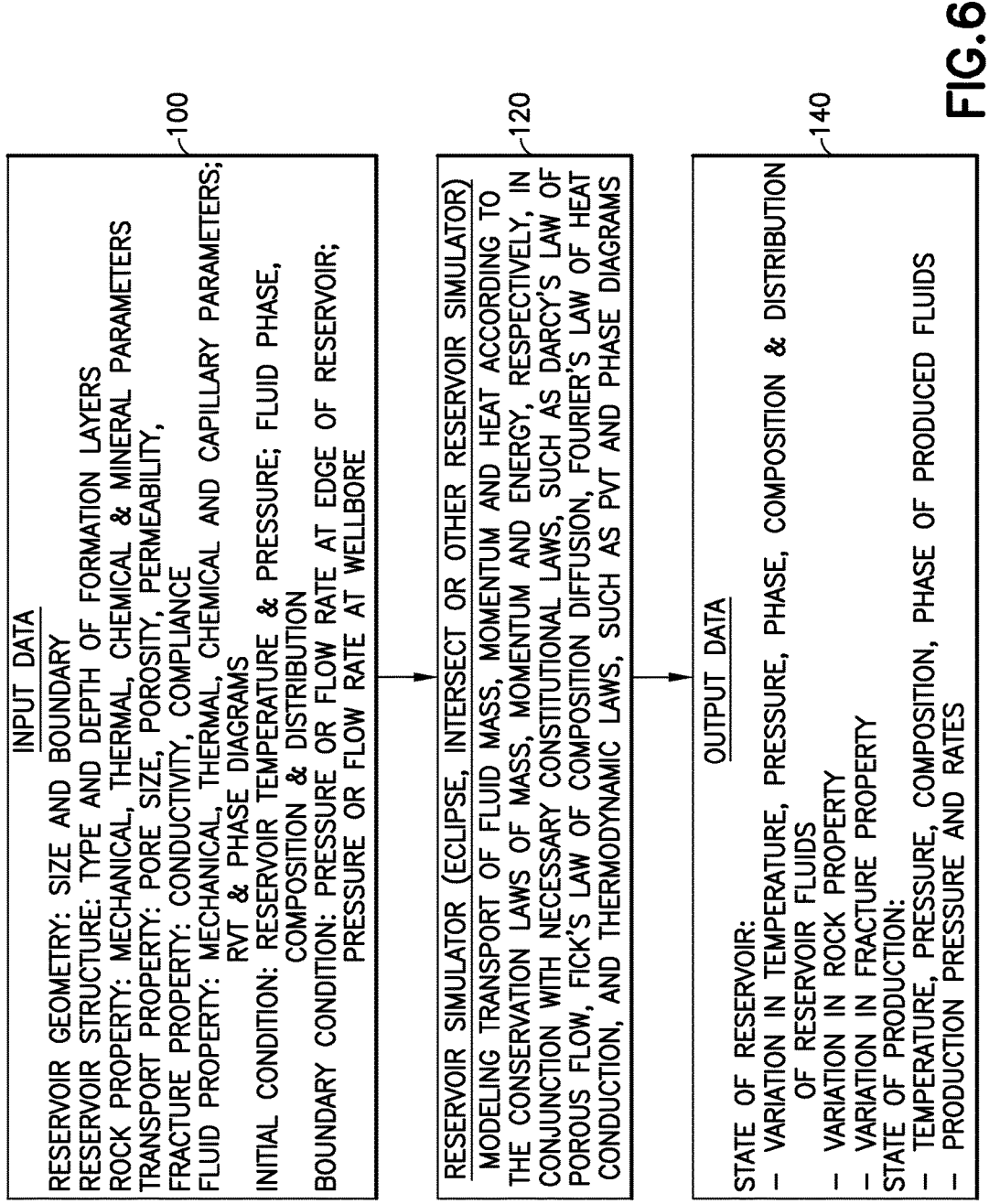
FIG. 6 is a flowchart showing a method of analyzing a shale gas reservoir for purposes of production of the gas.
Figure 7:
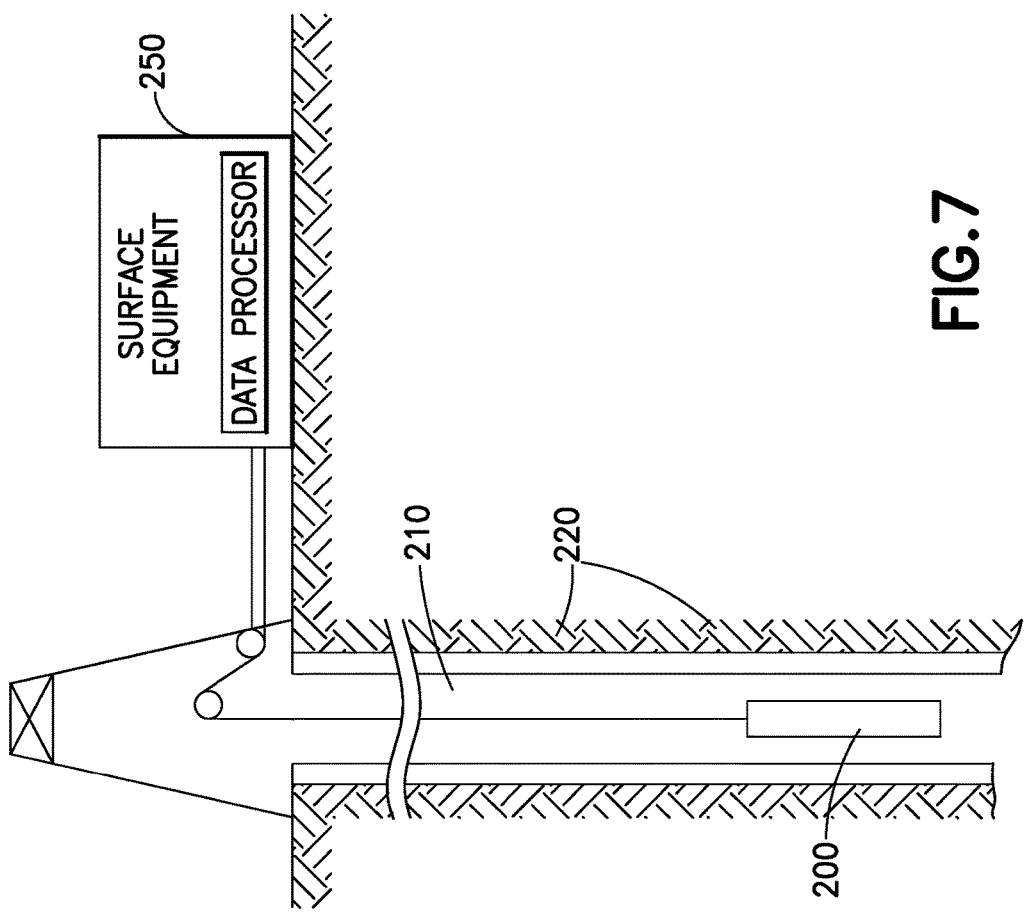
FIG. 7 represents a formation traversed by a wellbore.

Having described (1) how the conventional Darcy's law can be generalized and extended to account for gas adsorption/desorption, various modes of advective and diffusive transports and non-Darcy flow behavior, and (2) how non-Darcy flow behavior can be accounted for by either adding a separate equation of momentum conservation or by modifying the transport coefficient of the continuity equation according to the law of momentum conservation, and (3) accounting for the effect of heat transport on the adsorption/desorption and flow of shale gas by adding a separate equation of energy conservation, it will be appreciated that gas flow and transport in a shale reservoir can be properly calculated by simultaneously solving the transport equations, e.g., for mass, momentum and energy. More particularly, in one embodiment, and as seen in FIG. 6 at 100, information regarding a reservoir is gathered. The information may include data such as reservoir geometry (e.g., size and boundaries), reservoir structure (e.g., type and depth of formation layers), rock properties (e.g., mechanical, thermal, chemical and mineral parameters), transport properties (e.g., pore size, porosity, permeability), fracture properties (e.g., conductivity and compliance), fluid properties (e.g., mechanical, thermal, chemical and capillary parameters, PVT and phase diagrams), initial conditions (e.g., reservoir temperature and pressure, fluid phase, composition and distribution), and boundary conditions (e.g., pressure or flow rate at edge of reservoir, pressure or flow rate at wellbore). The information may be obtained as suggested by FIG. 7 through the use of one or more logging tools such as tool 200 which is located and moved in a borehole (wellbore) 210 traversing a formation of interest 220, and/or by tools located on the surface of the formation, or by any other suitable means available. The data obtained, e.g., from the tools, are processed by one or more processors 250 that are shown on the surface of the formation 220, but which may be located downhole with the tool(s) 200 or uphole on the formation surface, or even at remote locations, and provide the information regarding the reservoir. The information is provided at 120 (FIG. 6) to a reservoir simulator such as ECLIPSE or INTERSECT (a trademark of Schlumberger), or another reservoir simulator which may be implemented in one or more high speed computer(s) or processors that are programmed with Darcy's law equations that are generalized and extended to account for one or more of gas adsorption/desorption, various modes of advective and diffusive transports and non-Darcy flow behavior. In one embodiment, the Darcy's law equations are generalized and extended according to equation (6) as informed by equations (7), (12), or (19). In one embodiment, in addition, the reservoir simulator is provided with a separate equation of momentum conservation to account for non-Darcy flow behavior. In one embodiment, the separate equation of momentum conservation set forth in equations (25) and (26). In one embodiment, the reservoir simulator is provided with a modified transport coefficient for the continuity equation in order to account for non-Darcy flow behavior. In one embodiment, the modified transport coefficient for the continuity equation that accounts for non-Darcy flow behavior is set forth in equations (25) and (26) that defines a modified permeability. In one embodiment, the reservoir simulator is provided with an equation of energy conservation in order to account for the effect of heat transport on the adsorption/desorption and flow of shale gas. In one embodiment, the equation of energy conservation is equation (27). When provided with generalized and extended Darcy's laws, the reservoir simulator provides at 140 (FIG. 6) output information including one or both of the state of the reservoir and the state of (gas) production, including, e.g., the variation in temperature, pressure, phase, composition and distribution of reservoir fluids, the variation in rock properties, and the variation in fracture properties, and e.g., the temperature, pressure, composition and phase of produced fluids, and the production pressure and rates for the fluids.

Returning to FIG. 3, hypothetical outputs of a simulator are seen in FIG. 3 where the production enhancement due to release of adsorbed gas is suggested. Thus, it will be appreciated that by utilizing equations (2) together with equations (15) to (21) in the simulator instead of equation (1), hypothetical increases in the cumulative production of gas over time are expected in two wells (Well A and Well B). The predicted increase in production might be used in an actual development environment to help determine whether or not to develop a field and might also be used in selecting production parameters where the field is going to be developed, where the production enhancement due to molecular diffusion and wall effect is seen.

Similarly, FIG. 2, which shows a hypothetical graph of the ratio of the apparent permeability ($k_{app}$) obtained after accounting for the wall effect on both advective and diffusive transports (as in equation 12) to the intrinsic permeability (k), suggests that the expected gas permeability of the reservoir is greatly increased. As a result, production decisions, including the selection of production parameters for the field might be significantly altered. In some cases, the increase predicted might even be the difference between a decision to develop a field or a decision to not develop the field.

In one embodiment, an output of the simulator that has been provided with the extension of the conventional Darcy's law is a graph showing production over time (as in FIG. 3). The graph may be tangible (paper), or may be provided on a computer monitor or other electronic device. In another embodiment, an output of the simulator that has been provided with the extension of the conventional Darcy's law is a plot of variations in a property of the reservoir, or a plot of the temperature, pressure, or composition of the fluids in the reservoir. Again, the plot may be provided in tangible form, or may be provided on an electronic medium.

According to one aspect, the extension of the conventional Darcy's law to account for gas adsorption/desorption, various modes of diffusive transport and non-Darcy flow behavior, and the accounting for non-Darcy flow behavior by either providing a separate equation of momentum conservation or by modifying the transport coefficient of the continuity equation according to the law of momentum conservation, and the accounting for the effect of heat transport on the desorption and flow of shale gas by adding a separate equation of energy conservation, can be broadly applied for hydrocarbon production forecasting, surveillance and optimization. The (semi-) analytical solutions previously described are much more rigorously obtained for more flexible boundary conditions compared to the state-of-the-art solutions previously used by the industry. These solutions form a better foundation of various applications of type curve analysis or pressure transient analysis, for both conventional and unconventional reservoirs.

In one aspect, it is a great challenge for reservoir engineers dealing with hydraulically fractured reservoirs to carry out reservoir simulation tasks both accurately and efficiently. The previously described dual-porosity approach including a shape factor derived from the fundamental fluid transport equation with arbitrarily specified transient pressure for fluid in the fracture network provides such accuracy and efficiency, as it is a function of both space and time, and naturally evolves during reservoir production.

In one embodiment, gas flow and transport in a shale reservoir can be properly calculated by simultaneously solving the transport equations (for mass, momentum and energy). Various simplifications can be made depending on reservoir type and the way of production.

In one aspect, methods of the subject disclosure form the basis for both reservoir simulation and production surveillance/forecasting/optimization. More particularly, in one embodiment, a reservoir simulator that is provided with information regarding the formation and which is programmed with an apparent permeability defined by an equation such as equation (7), (12), (19) or (26) and/or with a mass conservation equation such as equation (55) having a dual-porosity shape factor defined according to equations (56)-(58) may be used to predict the state of the reservoir and/or the state of production of fluids for forecasting and/or optimization. Moreover, once production starts, additional data may be obtained regarding the formation (e.g., from sensors and/or logging tools) and provided to the formation simulator in order to update the simulator parameters and provide production surveillance.

Some of the methods and processes described above, including processes, as listed above, can be performed by a processor. The term "processor" should not be construed to limit the embodiments disclosed herein to any particular device type or system. The processor may include a computer system. The computer system may also include a computer processor (e.g., a microprocessor, microcontroller, digital signal processor, or general purpose computer) for executing any of the methods and processes described above.

The computer system may further include a memory such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), a PC card (e.g., PCMCIA card), or other memory device.

Some of the methods and processes described above can be implemented as computer program logic for use with the computer processor. The computer program logic may be embodied in various forms, including a source code form or a computer executable form. Source code may include a series of computer program instructions in a variety of programming languages (e.g., an object code, an assembly language, or a high-level language such as C, C++, or JAVA). Such computer instructions can be stored in a non-transitory computer readable medium (e.g., memory) and executed by the computer processor. The computer instructions may be distributed in any form as a removable storage medium with accompanying printed or electronic documentation (e.g., shrink wrapped software), preloaded with a computer system (e.g., on system ROM or fixed disk), or distributed from a server or electronic bulletin board over a communication system (e.g., the Internet or World Wide Web).

Alternatively or additionally, the processor may include discrete electronic components coupled to a printed circuit board, integrated circuitry (e.g., Application Specific Integrated Circuits (ASIC)), and/or programmable logic devices (e.g., a Field Programmable Gate Arrays (FPGA)). Any of the methods and processes described above can be implemented using such logic devices.

Although only a few examples have been described in detail above, those skilled in the art will readily appreciate that many modifications are possible in the examples without materially departing from this subject disclosure. Accordingly, all such modifications are intended to be included within the scope of this disclosure as defined in the following claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. § 112, paragraph 6 for any limitations of any of the claims herein, except for those in which the claim expressly uses the words 'means for' together with an associated function.

What is claimed is:

1. A method for analyzing a reservoir in a formation containing hydrocarbon fluid, comprising:
   collecting information characterizing the formation, said
      information collected from data obtained by at least one tool having interacted with the formation and processed to provide the information;

providing the information to a reservoir simulator incorporating a computational model of the formation that represents geological and fluid properties of the formation, the computational model including at least one equation representing transport of the hydrocarbon fluid through the formation using a permeability based on pore size and change in flow velocity over time; and running the reservoir simulator to generate a solution for exploiting the formation, wherein the solution includes indications of at least one of the state of the reservoir and the state of the production of hydrocarbon fluid from the reservoir in the formation.

2. A method according to claim 1, wherein:

the hydrocarbon fluid comprises hydrocarbon gas, and the formation comprises a shale matrix containing the hydrocarbon gas.

3. A method according to claim 2, wherein:

the at least one equation accounts for transport of the hydrocarbon gas through the shale matrix according to a first relationship $$\frac{\partial \omega}{\partial t} - \nabla \cdot (\kappa \nabla \omega) = 0,$$

where $\omega = \phi \rho_g$, t is a time index, $\phi$ is the porosity of the shale matrix, $\rho_g$ is the density of the hydrocarbon gas, and where $\kappa$ is the effective diffusivity defined according to $$\kappa = \frac{k_{app}}{\phi c_t \mu_g},$$

where $c_t$ is a total compressibility equal to a pore compressibility plus a gas compressibility, $\mu_g$ is the viscosity of the hydrocarbon gas, and $k_m$ is a permeability defined according to $$k_m = k_{app}\left(1 - \frac{k_{app}\rho_g}{\phi \mu_g v}\frac{Dv}{Dt}\right),$$

where $\rho_g$ is the density of the hydrocarbon gas, Dv/Dt is the change in flow velocity over time, and $k_{app}$ is an apparent permeability based on pore size.

4. A method according to claim 3, wherein:

said apparent permeability $k_{app}$ is defined according to $$k_{app} = k\left[1 + \frac{16 D_g \mu_g (1 + c_g p)}{d_p^2 p}\right],$$

where $c_g$ is said gas compressibility, p is the fluid pressure of the hydrocarbon gas, k is the intrinsic permeability of the shale matrix, $d_p$ is the effective pore size and $D_g$ is the molecular diffusivity, corresponding to the random thermal motion of gas molecules between their consecutive collisions to each other.

5. A method according to claim 3, wherein:

said apparent permeability $k_{app}$ is defined according to $$k_{app} = k\left[W_A(K_N) + \frac{16 D_g W_D(K_N)\mu_g(1 + c_g p)}{d_p^2 p}\right]$$

where $c_g$ is the gas compressibility, p is the fluid pressure of the hydrocarbon gas, k is the intrinsic permeability of the shale matrix, $d_p$ is the effective pore size, $D_g$ is the molecular diffusivity corresponding to the random thermal motion of gas molecules between their consecutive collisions to each other, and $W_A$ and $W_D$ are respectively advective and diffusive wall effect multipliers that are a function of the Knudsen number $K_N$ which is a function of the mean free path of the molecules of gas and the diameter of the pores of the shale matrix.

6. A method according to claim 5, wherein:

$$W_A(K_N) = \left[\frac{16}{3}\left(\frac{2}{\alpha} - 1\right)K_N + \left(1 - \frac{4}{3}K_N\right)^2\right]\left(1 - \frac{4}{3}K_N\right)^2 H\left(1 - \frac{4}{3}K_N\right),$$

where $\alpha$ is the fraction of diffuse reflection of molecules after their collision with pore wall and has a value close to 1, and $$K_N = \frac{\lambda}{d_p}$$

where $\lambda$ is the mean free path of hydrocarbon gas molecules defined as $$\lambda = \frac{2\sqrt{2}}{\pi \sigma^2 \rho_g} m_g \qquad (11)$$

where $m_g$ is the molecular mass and $\sigma$ is the diameter of the hydrocarbon gas molecules.

7. A method according to claim 6, wherein:

$$W_D(K_N) = \begin{cases} 1, & K_N \leq \frac{1}{2} \\ \frac{1}{2}E(K_N) + \frac{1}{4K_N}, & K_N > \frac{1}{2} \end{cases}$$

where $$E(K_N) = 1 - \left(1 - \frac{1}{4K_N^2}\right)^{3/2} + \frac{3}{4K_N^2}\left(\arcsin\frac{1}{2K_N} + \sqrt{4K_N^2 - 1} - \frac{\pi}{2}\right).$$

8. A method according to claim 3, wherein:

said apparent permeability $k_{app}$ is defined according to $$k_{app} = k\left[W_A(K_N) + \frac{16 D_g W_D(K_N)\mu_g(1 + c_g p)}{d_p^2 p}\right]\frac{\rho_g(1 - V_a)}{\rho}$$

where $c_g$ is the gas compressibility, p is the fluid pressure of the hydrocarbon gas, k is the intrinsic permeability of the shale matrix $d_p$ is the effective pore size, $D_g$ is the molecular diffusivity corresponding to the random thermal motion of hydrocarbon gas molecules between their consecutive collisions to each other, $W_A$ and $W_D$ are respectively advective and diffusive wall effect multipliers that are a function of the Knudsen number $K_N$ which is a function of the mean free path of the molecules of gas and the diameter of the pores of the formation, $V_a$ is the pore volume fraction of the formation, and $\rho$ is the collective density of the mixture of free and adsorbed hydrocarbon gas.

9. A method according to claim 8, wherein:
said total compressibility $c_t$ is given as $$c_t = \frac{\rho_g(c_g+c_\phi)}{\rho} + \frac{V_a}{\rho}\left[\rho_a c_a - \rho_g c_g + \frac{\rho_a - \rho_g}{(1+Bp)p}\right],$$

where $c_\phi$ and $c_g$ are respectively the pore compressibility and gas compressibility, $\rho_a$ and $V_a$ are respectively the density and the volume fraction of the adsorbed hydrocarbon gas, B is the relative life of a molecule of adsorbed hydrocarbon gas and $$c_a = \frac{1}{\rho_a}\frac{\partial \rho_a}{\partial p}$$

is the compressibility of the adsorbed hydrocarbon gas.

10. A method according to claim 3, wherein:
the at least one equation accounts for mass transport of the hydrocarbon gas through the shale matrix according to a second relationship $$\vec{v} = -\frac{k_m}{\mu_g}\nabla p,$$

where $\vec{v}$ is an apparent flow velocity vector, and p is the fluid pressure of the hydrocarbon gas.

11. A method according to claim 3, wherein:
the at least one equation accounts for heat transport of the hydrocarbon gas through the shale matrix according to a third relationship s $$\frac{\partial}{\partial t}[\phi\rho h + (1-\phi)\rho_s h_s] + \nabla \cdot (\rho_g h_g \vec{v} - \lambda \nabla T) = 0,$$

where $\lambda$ is the effective heat conductivity and T is the temperature of the hydrocarbon gas, $\rho_s$ and $h_s$ are the density and enthalpy of the shale matrix, $h_g$ is the enthalpy of the hydrocarbon gas, $\vec{v}$ is a flow velocity vector for the hydrocarbon gas, $\phi$ is the porosity of the shale matrix containing the hydrocarbon gas, and $\rho h = (1-V_a)\rho_g h_g + V_a\rho_a h_a$, and $\rho = (1-V_a)\rho_g + V_a\rho_a$ where $h_a$ is the enthalpy of adsorbed hydrocarbon gas and $V_a$ is the volume fraction of the adsorbed hydrocarbon gas.

12. A method according to claim 3, wherein:
the at least one equation accounts for mass conservation of hydrocarbon gas according to a fourth relationship $$\frac{\partial \omega_{fn}}{\partial t} - \frac{4}{\pi x h_{fn}}\frac{\partial}{\partial x}\left(x h_{fn}\kappa_{fn}\frac{\partial \omega_{fn}}{\partial x}\right) = \sigma \kappa_m(\omega_m - \omega_{fn}),$$

where, t is a time index, x is a coordinate index, $h_{fn}$ is the height of a fracture network, $\sigma$ is a shape factor, $\kappa_{fn}$ and $\kappa_m$ are respectively the fracture network effective diffusivity in the fracture network and an average matrix effective diffusivity, and $\omega_{fn}$ and $\omega_m$ are respectively fracture network and average matrix properties with $\omega_{fn}=\phi_{fn}\rho_g$ where $\phi_{fn}$ is the porosity of the fracture network and $\omega_m=\phi_m\rho_g$ where $\phi_m$ is the average matrix porosity, and $\rho_g$ is the density of the hydrocarbon gas.

13. A method according to claim 12, wherein:
said shape factor is defined by $$\sigma = \frac{6\sqrt{\pi\kappa_m}\sum_{n=0}^{\infty}C_n(L_1)a_n(t,L_1) - \frac{L_2+2L_1}{L_1}\sum_{n=0}^{\infty}b_n(t,L_1) - 6\sum_{n=0}^{\infty}f_n(t,L_1)}{\left[\begin{array}{c}\frac{L_2}{L_1}\sum_{n=0}^{\infty}\frac{f_n(t,L_1)}{C_n^2(L_1)} - 4\sqrt{\pi}\,\kappa_m^{3/2}\sum_{n=0}^{\infty}C_n(L_1)c_n(t,L_1) + \\ \frac{L_2+2L_1}{L_1}\kappa_m\sum_{n=0}^{\infty}d_n(t,L_1) + 4\kappa_m\sum_{n=0}^{\infty}e_n(t,L_1)\end{array}\right]}$$

where $$a_n(t,L_1) = \int_0^t \sqrt{t-u}\,\mathrm{erfc}\left[C_n(L_1)\sqrt{\kappa_m(t-u)}\,\right]\frac{d\omega_{fn}}{dt}\bigg|_{(u)}du$$

$$b_n(t,L_1) = \int_0^t Ei[-C_n^2(L_1)\kappa_m(t-u)]\frac{d\omega_{fn}}{dt}\bigg|_{(u)}du$$

$$c_n(t,L_1) = \int_0^t (t-u)^{3/2}\mathrm{erfc}\left[C_n(L_1)\sqrt{\kappa_m(t-u)}\,\right]\frac{d\omega_{fn}}{dt}\bigg|_{(u)}du$$

$$d_n(t,L_1) = \int_0^t (t-u)Ei[-C_n^2(L_1)\kappa_m(t-u)]\frac{d\omega_{fn}}{dt}\bigg|_{(u)}du$$

$$e_n(t,L_1) = \int_0^t (t-u)e^{-C_n^2(L_1)\kappa_m(t-u)}\frac{d\omega_{fn}}{dt}\bigg|_{(u)}du$$

and $$C_n(L_1) = \frac{(2n+1)\pi}{2L_1}$$

where L1 is half the spacing between fractures of the fracture network in a first direction and L2 is half the spacing between fractures of the fracture network in a second direction perpendicular to said first direction.

14. A method according to claim 2, wherein:
the at least one equation uses a property w which is based on a product of porosity of the shale matrix and density of the hydrocarbon gas.

15. A method according to claim 14, wherein:
the density of the hydrocarbon gas is based on volume fraction of adsorbed hydrocarbon gas.

16. A method according to claim 2, wherein:
the at least one equation uses at least one of i) an apparent permeability based on pore size of the shale matrix, ii) a multiplier factor to quantify effect of gas molecule collision on pore walls in the transport of the hydrocarbon gas, and iii) an effective compressibility based on pore size of the shale matrix.

17. A method according to claim 2, wherein:
the at least one equation assumes isothermal gas flow and does not account for the law of energy conservation.

18. A method according to claim 2, wherein:
the at least one equation does not assume isothermal gas flow and is based on the law of energy conservation.

19. A method according to claim 2, wherein:
the at least one equation accounts for absorption and desorption of the hydrocarbon gas.

20. A method according to claim 2, wherein:
the at least one equation accounts for non-Darcy flow behavior by providing a separate equation of momentum conservation or by providing a continuity equation with a transport coefficient based on the law of momentum conservation.

21. A method according to claim 2, wherein:
the at least one equation includes an equation of energy conservation that accounts for the effect of heat transport on desorption and flow of hydrocarbon gas.

22. A method according to claim 2, wherein:
the at least one equation models production of hydrocarbon gas from a single hydraulic fracture in the shale matrix to a wellbore as a function of time.

23. A method according to claim 2, wherein:
the at least one equation models production of hydrocarbon gas from a fracture network in the shale matrix to a wellbore as a function of time.

24. A method according to claim 1, wherein:
the solution comprises a graph indicating production of the hydrocarbon fluid from the formation over time.

25. A method according to claim 1, wherein:
the reservoir simulator comprises a processor.

\* \* \* \* \*